United States Patent [19]

Jacquelin et al.

[11] 4,332,866

[45] Jun. 1, 1982

[54] METHOD OF TEMPERATURE REGULATION

[75] Inventors: Jean Jacquelin, Malassis; Jean-Paul Pompon, Vitry, both of France

[73] Assignee: Societe Anonyme dite: Compagnie Generale D'Electricite, Paris, France

[21] Appl. No.: 226,546

[22] Filed: Jan. 21, 1981

[30] Foreign Application Priority Data

Jan. 22, 1980 [FR] France .................................. 80 01290

[51] Int. Cl.³ ...................... H01M 6/18; H01M 10/50
[52] U.S. Cl. ..................................... 429/50; 429/104; 429/120; 429/112
[58] Field of Search ................... 429/50, 52, 112, 120, 429/104, 101, 102

[56] References Cited

U.S. PATENT DOCUMENTS

| | | | |
|---|---|---|---|
| 3,404,035 | 10/1968 | Kummer et al. | 429/50 |
| 3,864,170 | 2/1975 | Krieger | 429/112 |
| 3,915,741 | 10/1975 | Kogiso et al. | 429/102 X |
| 3,976,503 | 8/1976 | Minck et al. | 429/50 |
| 4,086,396 | 4/1978 | Mathers et al. | 429/112 X |
| 4,087,591 | 5/1978 | Bowers et al. | 429/112 X |
| 4,246,325 | 1/1981 | Hatch | 429/50 |

FOREIGN PATENT DOCUMENTS 2414758 10/1975 Fed. Rep. of Germany .
2819600 11/1979 Fed. Rep. of Germany .
2301107 9/1976 France .

*Primary Examiner*—Anthony Skapars
*Attorney, Agent, or Firm*—Kenyon & Kenyon

[57] ABSTRACT

In a method of regulating the temperature of a system in which exothermic type reactions take place at temperatures of several hundreds of degrees and which are followed by stoppage periods, the system (1) is put in contact with a first substance (4) whose boiling temperature (T2) is close to the required temperature (T) of the system, and heat which results from the exothermic reactions is used to boil the first substance (4). Thereafter heat which comes from the condensation of the vapor evolved by said boiling is used to heat a second substance (5) to its melting point (T1), the second substance (5) being chosen so that it melts at a temperature close to but lower than the boiling temperature (T2) of the first substance (4). In operation the second substance (5) is kept at a temperature which is substantially constant and a little higher than its melting point (T1) until the end of a period of exothermic reaction. During the following period of stoppage the second substance (5) solidifies, whereby the temperature of the system is kept substantially constant until the end of the stoppage period. The method is useful in sodium/sulphur and lithium/iron sulphide electric battery systems.

6 Claims, 9 Drawing Figures

METHOD OF TEMPERATURE REGULATION

BACKGROUND OF THE INVENTION

The present invention relates to a method of temperature regulation. In systems where exothermic reactions take place and which operate at a determined temperature or within a determined temperature range (sometimes very much higher than ambient temperature) circumstances sometimes require both that the heat which results from said reactions should be dissipated and that heat should be introduced to the system, in particular to start it up initially and after temporary periods of stoppage.

This is the case in particular with sodium/sulphur electric batteries which require an operating temperature of about 300° C. to 360° C. and in which both the charging and the discharging processes result in the evolution of heat.

It is also the case of lithium/iron sulphide electric batteries in which the operating temperature is substantially 400° to 450° C.

The conventional method therefore consists in introducing external heat to the system to start it up and, vice versa, in dissipating the heat generated by the system during operation so as to keep its temperature at a nominal operating value.

However, the energy balance of such a method turns out to be very poor since it consumes an appreciable fraction of the energy supplied by the battery, whose efficiency is therefore impaired to the same extent.

SUMMARY OF THE INVENTION

The present invention mitigates this drawback by keeping a reactor within a regulated temperature range with reduced need to add energy from outside the system.

The invention provides a method of regulating the temperature of a system in which an exothermic reaction takes place intermittently at a temperature of at least one hundred degrees centigrade, said reaction taking place in a reactor and during reaction periods which are interspersed with periods of stoppage; the method comprising:

Keeping said system in thermal contact with a mass of a first substance chosen to have a boiling point close to the required temperature of the system; whereby heat resulting from said exothermic reaction causes said first substance to boil;

Keeping said first substance in thermal contact with a mass of a second substance chosen to have a melting point close to but less than the boiling point of the first substance, whereby heat derived from condensation of the vapour of the first substance causes said second substance to melt; and regulating the temperature of the second substance by adding heat thereto or removing heat therefrom as required to ensure that once all the second substance has melted during a period of exothermic reaction its temperature does not rise more than a few degrees above its melting point, and that once all the second substance has solidified during a stoppage period its temperature does not fall more than a few degrees below its melting point.

For a given system, e.g. traction batteries, the durations of the reaction periods (charging or discharging) and the durations of the intervening stoppage periods (standby) can often be forecast with reasonable accuracy. It is then a matter of calculation to determine what quantities of the particular first and second substances would be required to ensure that under normal circumstances heat need neither be dissipated nor added to the system.

BRIEF DESCRIPTION OF THE DRAWINGS

The following description is given by way of example with reference to the accompanying drawings and diagrams in which.

PRIOR ART

Figure 1:
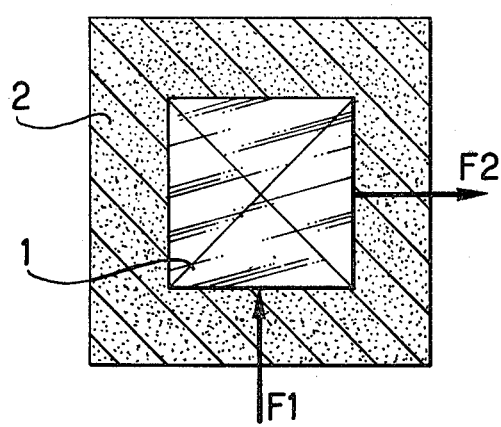
FIG. 1 illustrates a reactor regulated in accordance with the conventional method.

FIG. 1 illustrates a system such as a reactor or chamber 1 in which exothermic reactions take place at a temperature T and are followed by stoppage periods.

The reactor is surrounded by thermal insulation 2.

In a known manner, the temperature T is regulated firstly by introducing external heat $F_1$ during periods of stoppage and secondly by dissipating heat $F_2$ generated during said reactions. Such functions may be performed, for example, by means of heating resistance and by means of a flow of cooling air, respectively (not shown).

Figure 2A:
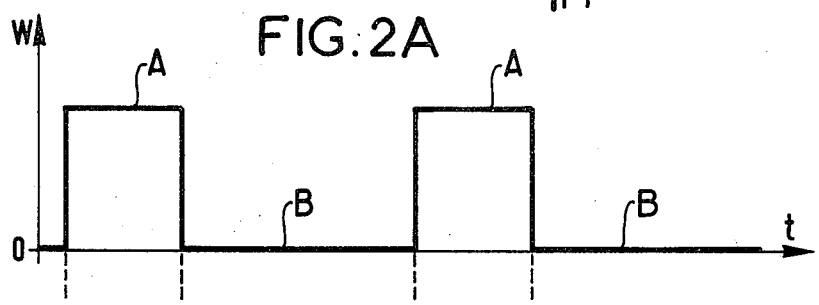
FIGS. 2A, 2B, 2C are diagrams which illustrate said conventional method.

FIG. 2A represents the heat energy W evolved by the reactor 1 as a function of time t in arbitrary units. The portions A of the curve correspond to exothermic reactions which occur in the reactor core while the portions B correspond to periods of time during which no energy is evolved.

Figure 2B:
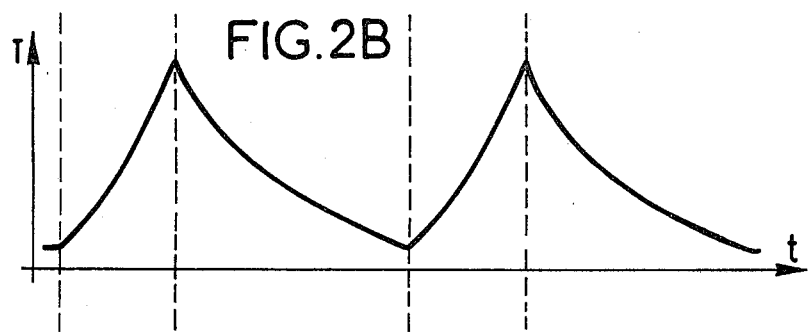

FIG. 2B shows the corresponding variations in temperature T of the reactor. It is seen that T oscillates and that the amplitude of its oscillations depends on the amount of the thermal insulation 2.

Figure 2C:
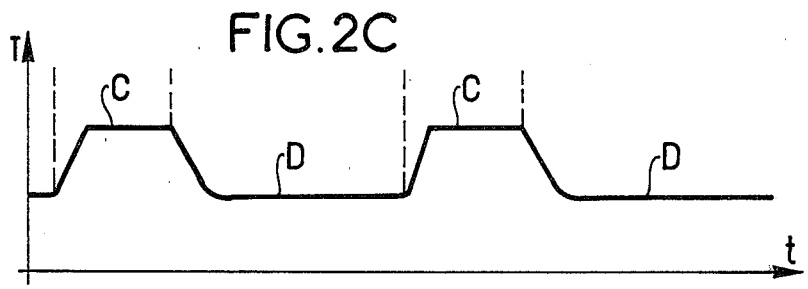

FIG. 2C shows oscillations of the temperature T using a conventional method of heat regulation. More precisely, portions C correspond to the dissipation of generated heat $F_2$ (FIG. 1) while portions D correspond to the application of external heat $F_1$. However, the oscillations of the temperature T still remain appreciable.

DESCRIPTION OF PREFERRED EMBODIMENTS

Figure 3:
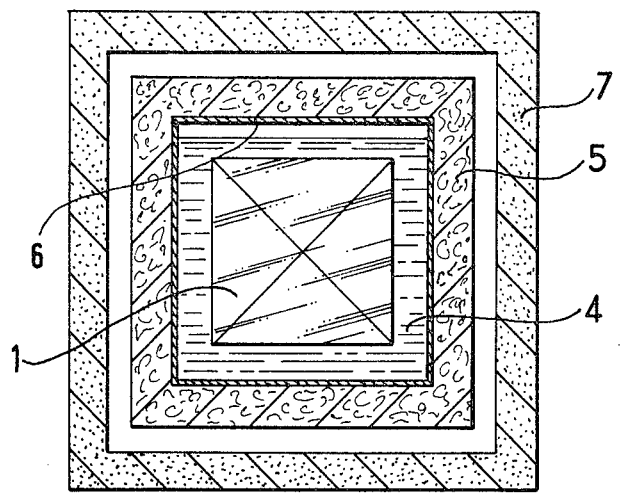
FIG. 3 illustrates a reactor regulated in accordance with the method of the invention.

FIG. 3 illustrates the reactor 1 regulated by the method in accordance with the invention.

To do this, said reactor 1 is disposed in a first substance 4 whose boiling point $T_2$ is close to the temperature T at which the reactor temperature is required to be set. This substance 4 can exchange heat directly with a second substance 5 via a heat-conducting partition 6 by means of the vapour which results from boiling the substance 4 condensing on said partition 6.

The assembly is disposed in a thermally insulating chamber 7. The melting point $T_1$ of the substance 5 is lower than the boiling point $T_2$ of the substance 4.

Of course, the substances 4 and 5 must be stable at the temperatures which prevail in the reactor and further, it is advantageous for them to be sufficiently pure for their phases to change at fixed temperatures.

Figure 4A:
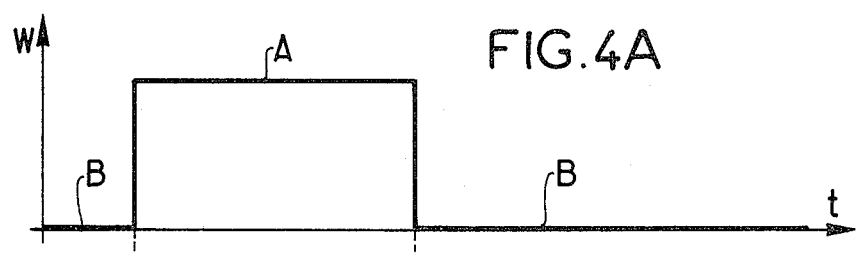
FIGS. 4A, 4B, 4C are diagrams which illustrate the method of the invention.

The operation of the method in accordance with the invention will now be explained:

FIG. 4A represents the heat energy W evolved within the reactor 1 as a function of time t in arbitrary units. The portion A of the curve corresponds to an exothermic reaction which takes place within the reactor, while the portions B correspond to periods of time in which no energy is evolved.

Figure 4B:
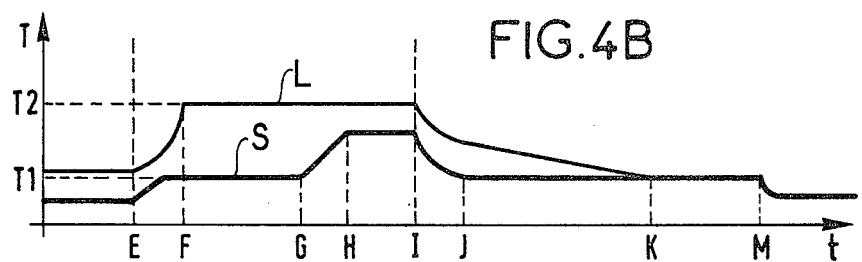

FIG. 4B shows the changes in temperatures of the first substance 4 (curve L) and of the second substance (curve I). Heat begins to evolve within the reactor at the time E and ends at the time S.

It is seen that during the time interval EF, the substance 4 heats up and reaches its boiling point $T_2$ while the substance 5 begins to melt after reaching its melting point $T_1$.

During the time interval FG the substance 4 continues to boil and the substance 5 continues to melt, melting ending at point G.

During the time interval GH, the substance 4 continues to boil while the temperature of the liquefied substance 5 increases. During the time interval HI, the substance 4 still continues to boil but the liquefied substance 5 is cooled by external means so that its temperature is stabilized at a value which lies between $T_1$ and $T_2$.

During the time interval IJ, the substance 4 ceases to boil and its temperature falls while the liquefied substance 5 cools down and begins to solidify at point J.

During the time interval JK the temperature of the substance 4 falls, while the substance 5 continues to solidify. At point K both substances are practically at the same temperature, namely, $T_1$ which is the melting point of the substance 5 and remain there until point M where the substance 5 has completely solidified and the temperature of both substances begins to fall. At that instant, the temperature of the substance 5 is kept close to but lower than $T_1$ by external means until further heat energy is evolved within the reactor.

Figure 4C:
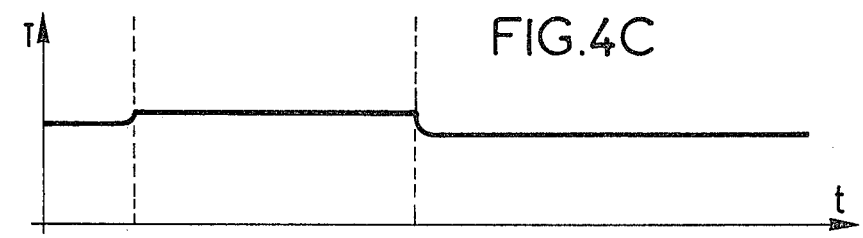

FIG. 4C shows that the temperature T oscillates with a small amplitude about an average value.

Further, if the assembly is required to be kept indefinitely at a temperature close to $T_1$, it is necessary to begin to supply external energy only from point M onwards as previously mentioned, while in the conventional method, such energy must be supplied from point I onwards. It is therefore seen that the method in accordance with the invention makes substantial energy saving possible with respect to time interval IM.

During normal system use, the interval IM should therefore be sufficient for a new operation cycle to being before point M is reached whereby extra external heat energy need never be supplied once the system has been started up. This reduces to a minimum the necessity of supplying extra external heat energy. (Clearly in a battery system external energy is supplied during recharging, and some of this energy is used in the form of heat; the point of the invention is to reduce requirements for extra energy beyond that which is used anyway during recharging.)

A concrete example will now be given of how to use the method in accordance with the invention in the case where the reactor 1 is a battery of sodium-sulphur electric cells which operate at a temperature of about 300° to 360° C.

The substance 4 may be a paraffin formed by a saturated hydro-carbon in which the number of carbon atoms lies between 17 and 23 so that the boiling point can be chosen to lie between 300° and 360° C.

The substance 5 can be either a pure substance or a eutectic.

By way of example, sodium thiocyanate, soda, hydrated potassium which contains 4% water or sodium nitrate can be used. The following systems whose melting points are shown in parentheses may be used as eutectics.

| | |
|---|---|
| KBr—KOH | (300° C.) |
| NaCl—CuCl | (314° C.) |
| KBr—MgBr$_2$ | (334° C.) |
| KBr—LiBr | (334° C.) |
| LiCl—KCl | (360° C.) |

In the case of a lithium/iron sulphide battery which operates at temperatures of about 400° to 450° C. the substance 4 may be for example a paraffin formed by saturated hydrocarbon which contains a number of atoms lying between 26 and 32.

The substance 4 may also be an isomer or a mixture of isomers of terphenyl, providing the system is subjected to a pressure of 2 to 5 atmospheres so that the boiling point can be chosen to lie between 400° and 450° C.

Advantageously and without limitation, the substance 5 may be chosen from among the following eutectics whose melting points are shown in parentheses:

| | |
|---|---|
| KCl—MnCl$_2$—NaCl | (400° C.) |
| CaCl$_2$—Ca(NO$_3$)$_2$ | (409° C.) |
| MgCl$_2$—NaCl | (430° C.) |
| KCl—MgCl | (430° C.) |
| KCl—ZnCl$_2$ | (433° C.) |
| CaCl$_2$—LiCl—NaCl | (440° C.) |
| KCl—MnCl$_2$ | (450° C.) |

Figure 5:
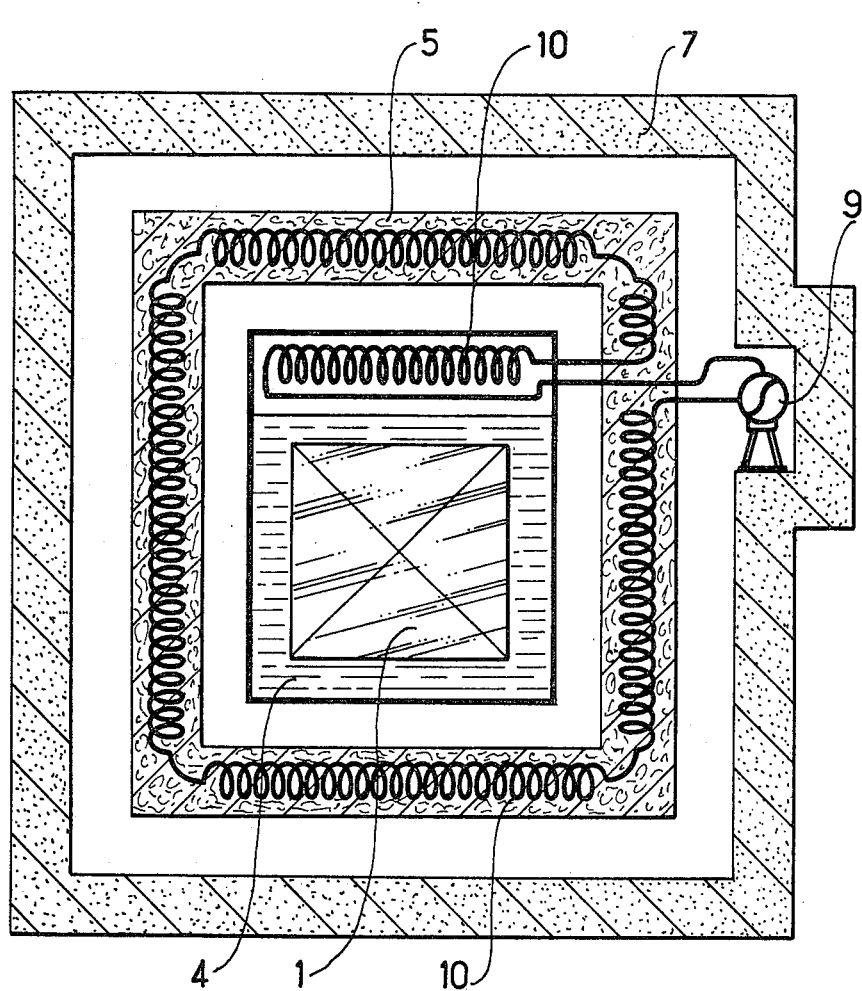
FIG. 5 illustrates a reactor regulated in accordance with a variant of the method of the invention.

FIG. 5 illustrates a reactor regulated in accordance with a variant of the method of the invention.

The reactor 1 is shown immersed in the substance 4.

The substance 5 is disposed at some distance from the tank which contains the substance 4, the whole being surrounded by the thermally insulating chamber 7.

However, this variant uses a heat-transfer liquid in thermal contact with the vapour of the substance 4.

For this purpose, a pump 9 circulates the heat transfer liquid in a closed circuit within the substance 5 via a heat exchanger 10.

Such an embodiment accelerates heat exchange between substances 4 and 5. In particular, this reduces internal temperature gradients.

Whatever embodiment is chosen, the method in accordance with the invention enables heat to be drawn from the reactor core and then progressively restored thereto so that the temperature of the reactor core fluctuates as little as possible.

It is particularly advantageous to apply the invention to sodium/sulphur and lithium/iron sulphide electric batteries used for traction purposes.

We claim:

1. A method of regulating the temperature of a system in which an exothermic reaction takes place intermittently at a temperature of at least one hundred degrees centigrade, said reaction taking place in a reactor and during reaction periods which are interspersed with periods of stoppage; the method comprising:

keeping said system in thermal contact with a mass of a first substance chosen to have a boiling point close to the required temperature of the system; whereby heat resulting from said exothermic reaction causes said first substance to boil;

keeping said first substance in thermal contact with a mass of a second substance chosen to have a melting point close to but less than the boiling point of the first substance, whereby heat derived from condensation of the vapour of the first substance causes said second substance to melt; and regulating the temperature of the second substance by adding heat thereto or removing heat therefrom as required to ensure that once all the second substance has melted during a period of exothermic reaction its temperature does not rise more than a few degrees above its melting point, and that once all the second substance has solidified during a stoppage period its temperature does not fall more than a few degrees below its melting point.

2. A method according to claim 1, wherein said regulated temperature lies substantially between 300° to 360°.

3. A method according to claim 1, wherein said regulated temperature lies substantially between 400° and 450°.

4. A method according to any one of claims 1 to 3, wherein heat is transferred from one of said substances to the other directly.

5. A method according to any one of claims 1 to 3, wherein heat is transferred from one of said substances to the other indirectly by means of a heat-transfer liquid.

6. A sodium/sulphur or lithium/iron sulphide battery system which is regulated using the method according to any one of claims 1 to 3.

* * * * *

UNITED STATES PATENT AND TRADEMARK OFFICE
CERTIFICATE OF CORRECTION

PATENT NO. : 4,332,866
DATED : June 1, 1982
INVENTOR(S) : Jean JACQUELIN and Jean-Paul POMPON It is certified that error appears in the above—identified patent and that said Letters Patent is hereby corrected as shown below:

Column 3, line 13: change "(curve I)" to --(curve S)--.

Column 3, line 14: change "S" to --I--.

Column 6, line 4: change "to" to --and--.

Signed and Sealed this

Tenth Day of August 1982

[SEAL]

Attest:

GERALD J. MOSSINGHOFF

Attesting Officer

Commissioner of Patents and Trademarks